United States Patent
Zhang et al.

(10) Patent No.: US 12,419,823 B2
(45) Date of Patent: Sep. 23, 2025

(54) ANTIMICROBIAL COMPOSITION

(71) Applicant: Solventum Intellectual Properties Company, Maplewood, MN (US)

(72) Inventors: Ying Zhang, Woodbury, MN (US); Robert A. Asmus, Hudson, WI (US); Zhicheng Tian, Woodbury, MN (US); Kheng Vang, St. Paul, MN (US); James P. Dizio, St. Paul, MN (US); Patrick J. Parks, Mendota Heights, MN (US); Brian E. Spiewak, Inver Grove Heights, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 975 days.

(21) Appl. No.: 17/600,010

(22) PCT Filed: Mar. 26, 2020

(86) PCT No.: PCT/IB2020/052891
§ 371 (c)(1),
(2) Date: Sep. 29, 2021

(87) PCT Pub. No.: WO2020/201945
PCT Pub. Date: Oct. 8, 2020

(65) Prior Publication Data
US 2022/0105018 A1 Apr. 7, 2022

Related U.S. Application Data

(60) Provisional application No. 62/827,281, filed on Apr. 1, 2019.

(51) Int. Cl.
*A61K 8/49* (2006.01)
*A61K 8/34* (2006.01)
*A61K 8/37* (2006.01)
*A61Q 17/00* (2006.01)
*A61K 8/41* (2006.01)

(52) U.S. Cl.
CPC ............ *A61K 8/4926* (2013.01); *A61K 8/342* (2013.01); *A61K 8/345* (2013.01); *A61K 8/375* (2013.01); *A61Q 17/005* (2013.01)

(58) Field of Classification Search
CPC ...... A61K 8/4926; A61K 8/342; A61K 8/345; A61K 8/375; A61K 8/37; A61K 8/416; A61Q 17/005
See application file for complete search history.

(56) References Cited

U.S. PATENT DOCUMENTS

| | | | |
|---|---|---|---|
| 5,084,096 A | 1/1992 | Stovicek |
| 5,408,022 A | 4/1995 | Imazato |
| 6,440,405 B1 | 8/2002 | Cooper |
| 8,569,384 B2 | 10/2013 | Asmus |
| 8,623,935 B2 | 1/2014 | Hobbs |
| 9,028,852 B2 | 5/2015 | Scholz |
| 2014/0294976 A1 | 10/2014 | Argembeaux |

FOREIGN PATENT DOCUMENTS

| | | | |
|---|---|---|---|
| EP | 3150234 | 4/2017 | |
| WO | WO2002-102244 | 12/2002 | |
| WO | WO2014-100807 | 6/2014 | |
| WO | WO-2014100807 A1 * | 6/2014 | ......... A61K 31/4425 |
| WO | WO2016-102132 | 6/2016 | |
| WO | WO2016-102133 | 6/2016 | |
| WO | WO-2020043269 A1 * | 3/2020 | ............ A01N 35/04 |
| WO | WO2020-240337 | 12/2020 | |

OTHER PUBLICATIONS

Yoshioka K, Nishimura H, Himukai M, Iwashima A. The inhibitory effect of choline and other quaternary ammonium compounds on thiamine transport in isolated rat hepatocytes. Biochim Biophys Acta. May 28, 1985;815(3):499-504. (Year: 1985).*
Wilson, Acetylcholine, McGraw Hill, 2022 (Year: 2022).*
PubChem, Glyceryl Monostearate, CID 24699, created 2005, https://pubchem.ncbi.nlm.nih.gov/compound/Glyceryl-Monostearate (Year: 2005).*
CAS STN search results, glyceryl stearate, entered 1984 (see attached) (Year: 1985).*
Block, Disinfection, Sterilization and Preservation, Chapter 13, 4th Edition, 1991, pp. 225-255.
International Search Report for PCT International Application No. PCT/IB2020/052891, mailed on Jun. 4, 2020, 5 pages.

* cited by examiner

*Primary Examiner* — Jeffrey H Murray
*Assistant Examiner* — Kevin S Martin

(57) ABSTRACT

Antimicrobial compositions containing an antimicrobial agent, such as an octenidine salt, a solubilizer, such as a glycol, and a cidatrope, such as a $C_8$-$C_{26}$ alcohol, an ether, an amide, an ester, and combinations thereof, where the compositions are substantially free of water and $C_2$-$C_5$ alcohols and methods of making such antimicrobial compositions.

19 Claims, No Drawings

ANTIMICROBIAL COMPOSITION

CROSS REFERENCE TO RELATED APPLICATIONS

This application is a national stage filing under 35 U.S.C. 371 of PCT/IB2020/052891, filed Mar. 26, 2020, which claims the benefit of Provisional Application No. 62/827,281, filed Apr. 1, 2019, the disclosures of each of which are incorporated by reference herein in their entireties.

TECHNICAL FIELD

The present disclosure relates to antimicrobial compositions containing an antimicrobial agent, a solubilizer, and a cidatrope, where the compositions are substantially free of water and $C_2$-$C_5$ alcohols.

BACKGROUND

It is standard practice in the industrialized world to apply an antiseptic preparation to the skin prior to any invasive procedure such as, for example, surgery, catheterization, or needle puncture, to reduce the risk of infection. Various antimicrobial agents, e.g., cationic antimicrobial agents, are established in the marketplace for use as a disinfectant and antiseptic for skin antisepsis before surgery and also for sterilizing surgical instruments and for cleaning wounds.

Some antimicrobial agents are used not only as an antiseptic to prevent hospital infections and as an adjuvant in oral hygiene, but also as a preservative in personal care products, such as, for example, antimicrobial dressings, skin preparations (e.g., lotions), bathing formulations, and nasal sprays.

SUMMARY

In one aspect, provided is an antimicrobial composition comprising 60 wt. % to 99.4 wt. % solubililzer, 0.1 wt. % to 10 wt. % antimicrobial agent and 0.1 wt. % to 15 wt. % cidatrope, wherein the composition is substantially free of water and a $C_2$-$C_5$ alcohol.

In another aspect, provided is a method of killing or inactivating microorganisms on a mammalian tissue, the method comprising contacting the mammalian tissue with an antimicrobial composition, the antimicrobial composition comprising 60 wt. % to 99.4 wt. % solubililzer, 0.1 wt. % to 10 wt. % antimicrobial agent, and 0.5 wt. % to 15 wt. % cidatrope, wherein the ready-to-use composition is substantially free of water and a $C_2$-$C_5$ alcohol.

Features and advantages of the present disclosure will be further understood upon consideration of the detailed description as well as the appended claims.

Definitions

As used herein, the term "ambient temperature" refers to the temperature range between about 21 and 25° C.

As used herein, the term "cidatrope" refers to a component in an antimicrobial composition that enhances the effectiveness of the antimicrobial composition such that when the antimicrobial composition less the antimicrobial agent and the composition less the cidatrope component are used separately, they do not provide the same level of antimicrobial activity as the antimicrobial composition including both the antimicrobial agent and the cidatrope. For example, a cidatrope component in the absence of the antimicrobial agent does not provide any appreciable antimicrobial activity. The enhancing effect can be with respect to the level of kill, the speed of kill, and/or the spectrum of microorganisms killed, and may not be seen for all microorganisms. The cidatrope component may be a synergist such that when combined with the remainder of the composition, the composition as a whole displays an activity that is greater than the sum of the activity of the composition less the cidatrope component and the composition less the antimicrobial agent. The cidatrope may be a solid or liquid at ambient temperature conditions As used herein, the term "dried composition" refers to a composition subjected to a process, e.g., heating, vacuum drying, whereby any volatile component that might be introduced to the composition during preparation has been removed such that the composition is substantially free of the volatile component.

As used herein, the term "nonvolatile" refers to a component that does not evaporate readily at ambient temperature conditions, such that a 20 g sample in a 4 cm$^2$ dish does not lose more than 2% of its weight within 60 minutes upon exposure to ambient temperature conditions. Examples of nonvolatile components of the compositions described herein include the disclosed antimicrobial agents, solubilizers, and cidatropes.

As used herein, the term "solvent" refers to any organic compound used to dissolve or disperse another compound.

As used herein, the term "surfactant" is synonymous with "emulsifier," and means an amphiphile (i.e., a molecule possessing both polar and nonpolar regions which are covalently bound) capable of reducing the surface tension of water and/or the interfacial tension between water and an immiscible liquid.

As used herein, the term "substantially free" means less than 1% by weight, less than 0.5% by weight, or less than 0.1% by weight, of a component based on the total weight of the composition.

As used herein the phrase "substantially free of water and a $C_2$-$C_5$ alcohol" refers to an antimicrobial composition free of water and a $C_2$-$C_5$ alcohol or an antimicrobial composition having less than 1% by weight, less than 0.5% by weight, or less than 0.1% by weight water and a $C_2$-$C_5$ alcohol, based on the total weight of the dried antimicrobial composition.

As used herein, the term "volatile" refers to a component that evaporates readily at ambient temperature conditions, such that a 20 g sample in a 4 cm$^2$ dish loses more than 2% of its weight within 60 minutes upon exposure to ambient temperature conditions. Examples of volatile components described herein include water and $C_2$-$C_5$ alcohols.

DETAILED DESCRIPTION

Provided herein are antimicrobial compositions containing an antimicrobial agent, a solubilizer, and a cidatrope, where the compositions are substantially free of water and $C_2$-$C_5$ alcohols. The compositions provided herein are formulations that provide rapid and persistent antimicrobial activity. The compositions described herein may be useful as preoperative surgical preps, hand antiseptics, dental antiseptics and varnishes, antimicrobial swabs, and wipes for skin disinfection. The compositions provided herein may be useful for preventing surgical site and catheter site infections when used as an antiseptic on the skin.

The compositions described herein display improved antimicrobial efficacy. Improved antimicrobial efficacy means a composition that exhibits any one or a combination of the following: (i) the composition maintains antimicrobial activity in the presence of the antimicrobial agent, despite the presence of a component that is known to affect the antimicrobial agent; (ii) the composition improves antimicrobial activity relative to the same composition without one of either the solubilizer or the cidatrope present; or (iii) the composition with less antimicrobial agent present maintains the same activity relative to a composition with more antimicrobial agent present but lacking one of either the solubilizer or the cidatrope; or (iv) the composition shows synergistic antimicrobial activity when the antimicrobial agent, solubilizer, and cidatrope are present.

The disclosed antimicrobial compositions have rapid bactericidal activity due to the enhanced activity of the antimicrobial agent in the presence of a solubilizer and a cidatrope. Such enhanced activity may allow for the use of lower concentrations of antimicrobial agents than would otherwise be possible, thus allowing for production of formulations having reduced risk of issues that may arise when higher concentrations of antimicrobial agents are used on human skin, such as, for example, skin sensitivity and/or irritation. Other benefits of the disclosed antimicrobial compositions including lower concentrations of antimicrobial agents than would otherwise be possible due to the enhanced activity of the antimicrobial agent in the presence of the solubilizer and cidatrope can include, for example, lower costs for production of the antimicrobial compositions and improved environmental impact (e.g., less antimicrobial agent ending up in waste-treatment facilities). The use of lower doses of antiseptic can carry an additional benefit of reducing or removing the possibility of antiseptic 'resistance' developing, where 'resistance' implies the requirement to use a higher amount of antimicrobial agent to achieve the same rate of microbial control.

The disclosed antimicrobial compositions can provide persistent bactericidal activity on the skin and may be non-irritating, particularly as they do not include chemical substances that can be skin irritants, such as, for example, $C_2$-$C_5$ alcohols or surfactants. The disclosed antimicrobial compositions may be particularly desirable in certain applications, such as, for example, as a component of a skin cream or baby oil, where the antimicrobial composition can also act as a barrier to retain skin moisture.

Antimicrobial Agents

Antimicrobial agents useful in embodiments of the present disclosure may include cationic antimicrobial agents. The cationic antimicrobial agent is that component of the composition that provides at least part of the antimicrobial activity. That is, the cationic antimicrobial agent has at least some antimicrobial activity for at least one microorganism, e.g. *Staphylococcus aureus*. The cationic antimicrobial agent is generally considered the main active component of the compositions described herein. The cationic antimicrobial agent includes an effective amount of one or more antimicrobial agents selected from the group consisting of biguanides and bisbiguanides, such as chlorhexidine and its various salts including, but not limited to, the digluconate, diacetate, dimethosulfate, and dilactate salts, as well as combinations thereof; polymeric quaternary ammonium compounds such as polyhexamethylenebiguanide; small molecule quaternary ammonium compounds such as benzalkonium halides, benzethonium halides, alkyl substituted benzethonium halides, cetyl pyridinium halides; and compatible combinations thereof. It is particularly important, however, with cationic antimicrobial agents in a salt form to use a counter ion that ensures solubility in aqueous fluid above the minimum inhibitory concentration ("MIC") of the treatment organism. If the solubility limit is less than the MIC, treatment may be ineffective.

The classes of cationic antimicrobial agent suitable in the present invention are discussed further below.

Biguanides

This class of antimicrobials is represented by the formula:

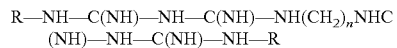

where n=3-10, preferably 4-8, and most preferably 6; and R.=$C_4$-$C_{18}$ branched or straight chain alkyl optionally substituted in available positions by halogen or $C_6$-$C_{12}$ aryl or alkaryl optionally substituted in available positions by a halogen.

In some embodiments, the preferred compound of this class is chlorhexidine. This may be present as the free base or as a disalt of acetate, gluconate, lactate, methosulfate ($CH_3OSO_3^-$), or a halide or combinations thereof. In some embodiments, the antimicrobial agent is chlorhexidine digluconate ("CHG"). Other anions may be useful.

Care must be taken when formulating chlorhexidine as well as other cationic antimicrobial compounds to avoid inactivation by sequestering it in micelles which may be formed by incorporation of surfactants and/or emulsifiers. Preferred compositions of this disclosure are substantially free of surfactants and/or emulsifiers.

Bis(biguanide)s such as chlorhexidine are very basic and capable of forming multiple ionic bonds with anionic materials. For this reason, biguanide-containing compositions are preferably free of anionic compounds that can result in precipitation of the antimicrobial. Anionic surfactants useful, for example, as wetting agents, may also need to be avoided. Halide salts may need to be avoided. For example, chlorhexidine digluconate ("CHG") will precipitate rapidly in the presence of halide salts above a concentration of about 0.1M. Therefore, if a system includes CHG or other antimicrobial of this class and needs to comprise salts for stability or other purposes, preferably gluconate salts such as triethanolamine gluconate or sodium gluconate, are used.

Polymeric Quaternary Amine Compounds

Antimicrobial polymers comprising quaternary amine groups may also be used as the cationic antimicrobial agent in the compositions described herein. These are typically polymers having quaternary amine groups with at least one alkyl or aralkyl chain of at least 6 carbon atoms and preferably as least 8 carbon atoms. The polymers may be linear, branched, hyperbranched or dendrimers. Preferred antimicrobial polymeric quaternary amine polymers include those described in U.S. Pat. Nos. 6,440,405; 5,408,022; and 5,084,096; PCT Publication No. WO/02102244; and Disinfection, Sterilization and Preservation, S. Block, 4$^{th}$ ed., 1991, Chapter 13, Lea & Febiger.

A particularly preferred class of polymeric quaternary ammonium antimicrobial compounds are polybiguanides. Compounds of this class are represented by the formula:

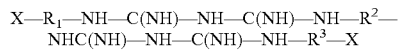

where $R^1$, $R^2$, and $R^3$ are bridging groups such as polymethylene groups preferably having 2 to 10 methylene groups, more preferably 4 to 8 methylene groups and most preferably 6 methylene groups. The methylene groups can be optionally substituted in available positions with halogen, hydroxyl, or phenyl groups. X is a terminal group and is typically an amine, amine salt, or a dicyandiamide group. The preferred compound of this class is polyhexamethylene biguanide ("PHMB")

commercially available as Cosmocil CQ from Aveci, Wilmington, Delaware, USA.

Poly(biguanide) antimicrobials such as PHMB are very basic and are capable of forming multiple ionic bonds with anionic materials. For this reason, biguanide-containing compositions are preferably free of anionic compounds that can result in precipitation and/or inactivation of the antimicrobial. Anionic surfactants useful, for example, as wetting agents, may also need to be avoided. Halide salts also may need to be avoided.

Small Molecule Quaternary Ammonium Compounds

This class of compounds typically comprise one or more quaternary ammonium groups wherein attached to the quaternary ammonium group is at least one $C_6$-$C_{18}$ linear or branched alkyl or aralkyl chain. Suitable compounds include those disclosed in Disinfection, Sterilization and Preservation, S. Block, 4$^{th}$ ed., 1991, Chapter 13, Lea & Febiger. Some compounds of this class have one or two $C_8$-$C_{18}$ alkyl or aralkyl chains and may be represented by the following formula:

$$R^1R^2NR^3R^{4+}X^-$$

where $R^1$ and $R^2$ are $C_1$-$C_{18}$ linear or branched alkyl, alkaryl, or aralkyl chains that may be substituted in available positions by N, O, or S provided at least one $R^1$ or $R^2$ is a $C_8$-$C_{18}$ linear or branched alkyl, alkaryl, or aralkyl chains that may be substituted in available positions by N, O, or S. $R^3$ and $R^4$ are $C_1$-$C_6$ alkyl, phenyl, benzyl, or $C_8$-$C_{12}$ alkaryl groups. $R^3$ and $R^4$ may also form a ring such as a pyridine ring with the nitrogen of the quaternary ammonium group. X is an anion, preferably a halide, and most preferably $C_1$— or Br—. Other anions may include methosulfate, ethosulfate, phosphates, and the like. Preferred compounds of this class include mnoalyltrimethylammonium salts, monalkyldimethylbenzyl ammonium salts, dialkyldimethyl ammonium salts, benzethonium chloride, and octenidine salts.

Examples of preferred quaternary ammonium antiseptics include benzalkonium halides having an alkyl chain length of $C_8$-$C_{18}$, more preferably $C_{12}$-$C_{16}$, and most preferably a mixture of chain lengths. For example, a typical benzalkonium chloride sample may be comprised of 40% $C_{12}$ alkyl chains, 50% $C_{14}$ alkyl chains, and 10% $C_{16}$ alkyl chains. These are commercially available from numerous sources, including Lonza (Barquat MB-50). Benzalkonium halides substituted with alkyl groups on the phenyl ring. A commercially available example is Barquat 4250 available from Lonza. Dimethyldialkylammonium halides where the alkyl groups have chain lengths of $C_8$-$C_{18}$. A mixture of chain lengths such as mixture of dioctyl, dilauryl, and dioctadecyl may be useful in some embodiments. Exemplary compounds are commercially available from Lonza as Bardac 2050, 205M, and 2250. Cetylpyridinium halides such as cetylpyridinium chloride available from Merrell labs as Cepacol Chloride. Benzethonium halides and alkyl substituted benzethonium halides such as Hyamine 1622 and Hyamine 10× available from Rohm and Haas. Octenidine salts such as, for example, octenidine dihydrochloride, octenidine gluconate, octenidine sulfate, octenidine acetate, and combinations thereof. Octenidine dihydrochloride is commercially available from TCI America, Portland, OR, USA.

For certain embodiments of the antimicrobial composition, the cationic antimicrobial agent is selected from the group consisting of chlorhexidine, chlorhexidine digluconate, chlorhexidine diacetate, chlorhexidine dimethosulfate, chlorhexidine dilactate salts, polyhexamethylenebiguanide, benzalkonium halides, octenidine salts, and combinations thereof. For certain preferred embodiments of the antimicrobial composition, the cationic antimicrobial agent is selected from the group consisting of octenidine dihydrochloride, octenidine gluconate, octenidine sulfate, octenidine acetate, and combinations thereof.

In some embodiments the antimicrobial agent is at least 0.01 wt. %, at least 0.025 wt. %, at least 0.05 wt. %, at least 0.1 wt. %, at least 0.25 wt. %, at least 0.5 wt. %, at least 1 wt. %, or at least 1.5 wt. % of the antimicrobial composition based on the total weight of the dried composition. In some embodiments the antimicrobial agent is commonly no more than 10 wt. %, no more than 9 wt. %, no more than 8 wt. %, no more than 7 wt. %, no more than 6 wt. %, no more than 5 wt. %, no more than 4 wt. %, or no more than 3 wt. % of the antimicrobial composition based on the total weight of nonvolatile components in the composition. In some embodiments the antimicrobial agent is commonly 0.01 wt. % to 10 wt. %, 0.025 wt. % to 9 wt. %, 0.05 wt. % to 8 wt. %, 0.1 wt. % to 7 wt. %, 0.25 wt. % to 6 wt. %, 0.5 wt. % to 5 wt. %, 1 wt. % to 4 wt. %, or 1.5 wt. % to 3 wt. % of the antimicrobial composition based on the total weight of nonvolatile components in the composition.

Solubilizer

The solubilizer functions in antimicrobial compositions of the present disclosure primarily as a solvent for the antimicrobial agent and the cidatrope. Preferably, the solubilizer is non-toxic and non-irritating to human skin.

Solubilizers suitable for use in compositions of the present disclosure include glycols (compounds having at least two hydroxyl groups per molecule) such as PEGs having a molecular weight below 2000 and preferably less than 1000 and most preferably less than about 800 daltons; glycerin and polyglycerols, propylene glycol, dipropylene glycol, tripropylene glycol, polypropylene glycol, ethylene oxide/propylene oxide random or block copolymers, ethoxylated polyhydric alcohols, trimethylolpropane, pentaerithiritol, sorbitol, panetothenol, glucuronolactone, gluconic acid, and the like as well as other polar solvents such as N-methylpyrrolidone, propylene carbonate, butyrolactone, and the like.

In some embodiments, the solubilizer may include glyceryl monoisostearate, glyceryl monooleate, decagylcerol hexaoleate, decagylcerol decaoleate, and combinations thereof.

In some embodiments the solubilizer is at least 60 wt. %, at least 65 wt. %, at least 70 wt. %, or at least 75 wt. % of the antimicrobial composition based on the total weight of the dried composition. In some embodiments the solubilizer is commonly no more than 99.4 wt. %, no more than 95 wt. %, no more than 90 wt. %, or no more than 85 wt. %, of the antimicrobial composition based on the total weight of nonvolatile components in the composition. In some embodiments the solubilizer is commonly 60 wt. % to 99.4 wt. %, 65 wt. % to 95 wt. %, 70 wt. % to 90 wt. %, or 75 wt. % to 85 wt. % of the antimicrobial composition based on the total weight of nonvolatile components in the antimicrobial composition.

Cidatrope

Cidatropes suitable for use in antimicrobial compositions of the present disclosure include $C_8$-$C_{26}$ alcohols, ethers, amides, esters, and combinations thereof. In some embodiments, the $C_8$-$C_{26}$ alcohol cidatrope is selected from the group consisting of 1-tetradecanol, hexadecanol, 16-methyl-1-heptadecanol, and combinations thereof. In some embodiments, the ether cidatrope is a propoxylated $C_2$ to $C_{18}$ alcohol having a degree of propoxylation of 2 to 50 moles per mole of alcohol. In some embodiments, the amide cidatrope is selected from the group consisting of a coconut fatty acid monoethanol amide, a coconut fatty acid methyl ethanolamide, an alkyl alkanolamide, and combinations thereof. In some embodiments, the ester cidatrope is selected from the group consisting of diisopropyl adipate, dibutyl sebacate, triethyl citrate, tributyl citrate, acetyltributyl citrate, octyldodecyl neopentanoate, laureth-2-acetate, isopropyl myristate, trioctyldodecyl citrate, myristyl myristate, cetyl acetate, and combinations thereof.

In some embodiments, the cidatrope is at least 0.1 wt. %, at least 0.5 wt. %, at least 1 wt. %, or at least 1.5 wt. % of the antimicrobial composition based on the total weight of the dried composition. The cidatrope is commonly no more than 15 wt. %, no more than 10 wt. %, no more than 8 wt. %, no more than 4 wt. % of the antimicrobial composition based on the total weight of nonvolatile components in the composition. The cidatrope is commonly 0.1 wt. % to 15 wt. %, 0.5 wt. % to 10 wt. %, 1 wt. % to 8 wt. %, or 1.5 wt. % to 4 wt. % of the antimicrobial composition based on the total weight of nonvolatile components in the antimicrobial composition.

In some embodiments, the cidatrope may also function as a solubilizer in antimicrobial compositions of the present disclosure, either as the sole solubilizer in the antimicrobial composition or as a solubilizer used in combination with another solubilizer as disclosed above. In such embodiments, the cidatrope doubling as a solubilizer may be more than 15 wt. %, more than 20 wt. %, more than 30 wt. %, more than 40 wt. %, more than 50 wt. % or more that 60 wt. % of the antimicrobial composition based on the total weight of nonvolatile components in the antimicrobial composition. In some embodiments, a cidatrope that also functions as a solubilizer may be a substituted citrate, such as, for example, acetyltributyl citrate.

In some embodiments, the weight percentage of cidatrope:antimicrobial agent in the antimicrobial composition based on the total weight of nonvolatile components in the antimicrobial composition is 0.1:1 to 150:1, such as, for example, 0.1:1, 0.25:1, 0.5:1, 0.75:1, 1:1, 1.25:1, 1.5:1, 2:1, 3:1, 4:1, 5:1, 6:1, 7:1, 8:1, 9:1, or 10:1, 15:1. 20:1, 25:1, 30:1, 35:1, 40:1, 45:1, 50:1, 60:1, 70:1, 80:1, 90:1, 100:1, 110:1, 120:1, 130:1, 140:1, or 150:1.

Antimicrobial Compositions

Antimicrobial compositions of the present disclosure may be prepared by methods known in the art using the components in amounts as described above. For example, the antimicrobial agent, solubilizer, and cidatrope may be combined, either stepwise or all at once, in a suitable container to provide a mixture. In some embodiments, the antimicrobial agent, solubilizer, and cidatrope may be combined at room temperature (e.g., 23° C.). In some embodiments, one or more of the antimicrobial agent, solubilizer, and cidatrope may be heated and/or melted before combination with other components of the antimicrobial composition. The mixture may be stirred or otherwise agitated for a period of time (e.g., 24 hours) to provide a homogenous antimicrobial composition. As disclosed above, preferred antimicrobial compositions of this disclosure are substantially free of surfactants and/or emulsifiers.

Antimicrobial compositions of the present disclosure may be useful to prevent hospital infections as a preoperative surgical, catheter, or intravenous site disinfectant, as an adjuvant in oral hygiene, and in personal care products, such as, for example, antimicrobial dressings, skin preparations (e.g., lotions), bathing formulations, and nasal sprays.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

| Material | Source |
| --- | --- |
| Glyceryl monoisostearate | Croda, Edison, NJ, USA |
| Glyceryl monooleate | Croda, Edison, NJ, USA |
| PRISORINE (3515-LQ) | Croda, Edison, NJ, USA |
| ARLAMOL (PC 10-AQ) | Croda, Edison, NJ, USA |
| Diisopropyl adipate | TCI America, Portland, OR, USA |
| Dibutyl sebacate | Spectrum, New Brunswick, NJ, USA |
| Triethyl citrate | Morflex, INC, Greensboro, NC, USA |
| Tributyl citrate | Spectrum, New Brunswick, NJ, USA |
| Myristyl alcohol | Spectrum, New Brunswick, NJ, USA |
| Glycerol | Croda, Edison, NJ, USA |
| Propylene glycol dipelargonate | Henkel Corporation, Dusseldorf, Germany |
| Octyldodecyl neopentanoate | Alzo, Sayreville, NJ, USA |
| Pelemol L2A | Phoenix Chemicals, Branchburg, NJ, USA |
| Isopropyl Myristate | Cognis, North Rhine-Westphalia, Germany |
| Trioctyldodecyl citrate | Alzo, Sayreville, NJ, USA |
| Propylene glycol isostearate | Henkel Corporation, Dusseldorf, Germany |
| Myristyl myristate | Croda, Edison, NJ, USA |
| Cetyl acetate | Phoenix Chemicals, Branchburg, NJ, USA |
| PPG-10-Butanediol | Croda, Edison, NJ, USA |
| Jarcol I-18 CG | Jarchem Industries, Newark, NJ, USA |
| Octenidine dihydrochloride | TCI America, Portland, OR, USA |
| Trypticase Soy Agar | Becton Dickinson, Franklin Lakes, NJ, USA |
| DIFCO Neutralizing Buffer | Becton Dickinson, Franklin Lakes, NJ, USA |
| Butterfields Buffer | 3M Company, Maplewood, MN, USA |

Testing Methods

Antimicrobial Testing—Direct Time Kill Test

The Direct Time Kill Test may be used to assess the in vitro reduction of aerobic microbial populations after exposure to a test material for a given amount of time. The time is either 2, 5, or 10 minutes in the present Examples 1 and 2. The test material is neutralized at the sampling time and the surviving microorganisms are enumerated. The Direct Time Kill test is based on ASTM E 2315-03 (Reapproved 2008). The detailed procedure is described below.

Sample Preparation

All test solutions are prepared and tested in triplicate. Using aseptic technique, a 1 mL test solution sample prepared as described below is placed in a sterile 50 mL conical tube for testing.

Testing Procedure

A bacterial suspension (about $10^8$ cfu/mL) is prepared from an 18-24 hour Staphylococcus aureus ATCC 6538 Trypticase Soy Agar culture plate using a 0.5 McFarland turbidity standard. 100 μL of the bacterial suspension is added to the 50 mL conical tube containing the 1 mL test solution sample, followed by an immediate 5 seconds of vortex. The inoculated test solution sample is left to incubate at room temperature (about 23° C.) for 2, 5, or 10 minutes.

After incubation, 40 mL of 2× concentration DIFCO Neutralizing Buffer is added to the test sample and the mixture is vortexed for a minimum of 30 seconds. Enumeration of the test samples is performed by serial ten-fold dilutions in Butterfields Buffer. After dilution, 1 mL from each dilution is plated in duplicate with about 15 mL of molten trypticase soy agar (tempered at about 45° C.) poured and added into the plate. The plate is then swirled to ensure mixing of the trypticase soy agar and 1 mL sample and allowed to solidify before incubation at 35° C. for 24-48 hours. After incubation, plates are counted and recorded.

Calculations

The colony-forming units ("CFU") recovered from each sample are calculated using plates with counts from 30-300 CFU per plate. The CFU counts are then averaged between the sample duplicate plates and $\log_{10}$ transformed to achieve the $\log_{10}$ recovery per sample. The sample $\log_{10}$ reduction is calculated by subtracting the $\log_{10}$ recovery of each sample from the average log recovery of the control or positive control samples (control/positive control n=3). The final average $\log_{10}$ reduction of each test material is achieved by averaging the triplicate sample log reductions.

Example 1

Solution Sample 1 is prepared as follows: Melted glyceryl monoisostearate (12.50 g) is added to a 20 ml vial, followed by triethyl citrate (2.25 g) and octenidine dihydrochloride (0.25 g). The vial is agitated on a roller for 24 hours at room temperature (e.g., 23° C.) resulting in a homogenous solution. Sample 2 and Comparative Example 1 ("CE-1") were prepared following a similar procedure, but with ARLAMOL in Solution Sample 2 instead of triethyl citrate and no cidatrope in CE-1.

Solution Samples 1 and 2 and CE-1 were used to carry out Direct Time Kill Tests as described above. Results are shown in Table 1.

TABLE 1

Direct Time Kill Test Results

| Solution Sample | Octenidine Dihydrochloride wt. % | Glyceryl Monoisostearate wt. % | Cidatrope | Cidatrope wt. % | 2-Minute Log Reduction | 5-Minute Log Reduction | 10-Minute Log Reduction |
|---|---|---|---|---|---|---|---|
| 1 | 1.7% | 83.3% | Triethyl citrate | 15 | 0.46 | 1.09 | 1.98 |
| 2 | 1.7% | 83.3% | ARLAMOL | 15 | 0.79 | 0.86 | 1.48 |
| CE-1 | 1.7% | 98.3% | — | 0 | 0.43 | 0.92 | 0.90 |

As the data in Table 1 show, samples including a cidatrope achieved higher log reduction of *Staphylococcus aureus* ATCC 6538 after 10 minutes than control CE-1 without cidatrope.

Example 2

Solution Samples 3-39, and CE-2 are prepared following the procedure described in Example 1, but with various cidatropes or no cidatrope as indicated in Table 2. Solution Samples 3-21, and CE-2 are were used to carry out Direct Time Kill Tests as described above. Results are shown in Table 2.

TABLE 2

Direct Time Kill Test Results

| Solution Sample | Octenidine Dihydrochloride wt. % | Glyceryl Monoisostearate wt. % | Cidatrope | Cidatrope wt, % | 10-Minute Log Reduction |
|---|---|---|---|---|---|
| 3 | 1.7 | 83.3 | ARLAMOL | 15 | 0.67 |
| 4 | 1.7 | 83.3 | PRISORINE | 15 | 1.41 |
| 5 | 1.7 | 83.3 | Glyceryl monooleate | 15 | 0.32 |
| 6 | 1.7 | 83.3 | Glycerol | 15 | 1.10 |
| 7 | 1.7 | 83.3 | Diiisopropyl adipate | 15 | 2.60 |
| 8 | 1.7 | 83.3 | Dibutyl sebacate | 15 | 1.67 |
| 9 | 1.7 | 83.3 | Triethyl citrate | 15 | 2.78 |
| 10 | 1.7 | 83.3 | Tirbutyl citrate | 15 | 0.76 |
| 11 | 1.7 | 83.3 | Myristyl alcohol | 15 | 1.93 |
| 12 | 1.7 | 83.3 | Propylene glycol dipelargonate | 15 | 0.61 |
| 13 | 1.7 | 83.3 | Octyldodecyl neopentanoate | 15 | 0.78 |
| 14 | 1.7 | 83.3 | Pelemol L2A | 15 | −0.02 |
| 15 | 1.7 | 83.3 | Isopropyl Myristate | 15 | 2.39 |
| 16 | 1.7 | 83.3 | Trioctyldodecyl citrate | 15 | 1.47 |
| 17 | 1.7 | 83.3 | Propylene glycol isostearate | 15 | 1.00 |

TABLE 2-continued

Direct Time Kill Test Results

| Solution Sample | Octenidine Dihydrochloride wt. % | Glyceryl Monoisostearate wt. % | Cidatrope | Cidatrope wt, % | 10-Minute Log Reduction |
|---|---|---|---|---|---|
| 18 | 1.7 | 83.3 | Myristyl myristate | 15 | 1.69 |
| 19 | 1.7 | 83.3 | Cetyl acetate | 15 | 1.62 |
| 20 | 1.7 | 83.3 | PPG-10-Butanediol | 15 | 1.99 |
| 21 | 1.7 | 83.3 | Jarcol I-18CG | 15 | 0.98 |
| CE-2 | 1.7 | 98.3 | — | 0 | 0.65 |

As shown in Table 2, samples with cidatrope, except those including glyceryl monooleate, Pelemol L2A, and propylene glycol dipelargonate, demonstrate higher 10-minutes log reduction of *Staphylococcus aureus* than the control sample, CE-2, without cidatrope included.

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. An antimicrobial composition comprising:
    60 wt. % to 99.4 wt. % solubilizer, the solubilizer selected from glyceryl monoisostearate, glyceryl monooleate, decagylcerol hexaoleate, decagylcerol decaoleate, and a combination thereof;
    0.1 wt. % to 10 wt. % antimicrobial agent, the antimicrobial agent selected from octenidine dihydrochloride, octenidine gluconate, octenidine sulfate, octenidine acetate, and a combination thereof; and
    0.1 wt. % to 15 wt. % cidatrope, the cidatrope selected from diisopropyl adipate, dibutyl sebacate, triethyl citrate, acetyltributyl citrate, trioctyldodecyl citrate, PPG-10 butanediol, and a combination thereof,
    wherein the composition is substantially free of water and a $C_2$-$C_5$ alcohol.
2. The antimicrobial composition of claim 1, wherein the solubilizer is glyceryl monoisostearate.
3. The antimicrobial composition of claim 1, wherein the cidatrope is diisopropyl adipate, dibutyl sebacate, or a combination thereof.
4. The antimicrobial composition of claim 1, wherein the cidatrope is selected from diisopropyl adipate, dibutyl sebacate, triethyl citrate, PPG-10 butanediol, and a combination thereof.
5. The antimicrobial composition of claim 1, wherein the cidatrope is selected from the group consisting of triethyl citrate, acetyltributyl citrate, trioctyldodecyl citrate, and a combination thereof.
6. The antimicrobial composition of claim 1, wherein the antimicrobial agent is octenidine dihydrochloride.
7. The antimicrobial composition of claim 1, wherein the cidatrope and antimicrobial agent are present at a weight ratio of 8:1 to 10:1 cidatrope:antimicrobial agent.
8. The antimicrobial composition of claim 7, wherein the solubilizer is glyceryl monoisostearate.
9. The antimicrobial composition of claim 8, wherein the cidatrope selected from triethyl citrate, acetyltributyl citrate, trioctyldodecyl citrate, and a combination thereof.
10. The antimicrobial composition of claim 8, wherein the cidatrope is selected from diisopropyl adipate, dibutyl sebacate, triethyl citrate, PPG-10 butanediol, and a combination thereof.
11. The antimicrobial composition of claim 7, wherein the solubilizer is glyceryl monoisostearate and the antimicrobial agent is octenidine dihydrochloride.
12. The antimicrobial composition of claim 7, wherein the cidatrope selected from triethyl citrate, acetyltributyl citrate, trioctyldodecyl citrate, and a combination thereof.
13. The antimicrobial composition of claim 7, wherein the cidatrope is selected from diisopropyl adipate, dibutyl sebacate, triethyl citrate, PPG-10 butanediol, and a combination thereof.
14. The antimicrobial composition of claim 1, wherein the solubilizer is glyceryl monoisostearate.
15. The antimicrobial composition of claim 1, wherein the solubilizer is glyceryl monoisostearate and the antimicrobial agent is octenidine dihydrochloride.
16. A personal care product comprising the antimicrobial composition of claim 1.
17. The personal care product of claim 16, wherein the personal care product is selected from the group consisting of an antimicrobial dressing, a skin preparation, a bathing formulation, and a nasal spray.
18. A method of killing or inactivating microorganisms on a mammalian tissue, the method comprising:
    contacting the mammalian tissue with an antimicrobial composition of claim 1.
19. The method of claim 18, wherein the solubilizer is glyceryl monoisostearate and the antimicrobial agent is octenidine dihydrochloride.

* * * * *